(12) United States Patent
Jou et al.

(10) Patent No.: US 10,598,547 B1
(45) Date of Patent: Mar. 24, 2020

(54) DEVICE FOR MEASURING MELATONIN SUPPRESSION INDUCED BY LIGHT SOURCE

(71) Applicant: National Tsing Hua University, Hsinchu (TW)

(72) Inventors: Jwo-Huei Jou, Hsinchu (TW); Meenu Singh, New Delhi (IN); Hsin-Fa Lin, Kaohsiung (TW)

(73) Assignee: National Tsing Hua University (TW)

( * ) Notice: Subject to any disclaimer, the term of this patent is extended or adjusted under 35 U.S.C. 154(b) by 0 days.

(21) Appl. No.: 16/158,514

(22) Filed: Oct. 12, 2018

(51) Int. Cl.
*G01J 3/02* (2006.01)
*G01J 3/12* (2006.01)
*G01J 3/457* (2006.01)
*A61M 21/00* (2006.01)

(52) U.S. Cl.
CPC ........... *G01J 3/0275* (2013.01); *A61M 21/00* (2013.01); *G01J 3/0264* (2013.01); *G01J 3/12* (2013.01); *G01J 3/457* (2013.01)

(58) Field of Classification Search
CPC .......... G01J 3/0275; G01J 3/0264; G01J 3/12; G01J 3/457; A61M 21/00
See application file for complete search history.

(56) References Cited

U.S. PATENT DOCUMENTS

| | | | | |
|---|---|---|---|---|
| 7,520,607 B2 * | 4/2009 | Casper | .................. | A61M 21/00 351/159.65 |
| 8,164,844 B2 * | 4/2012 | Toda | ..................... | A61M 21/02 359/589 |
| 2001/0056293 A1 * | 12/2001 | Brainard | .............. | A61N 5/0618 607/88 |
| 2005/0236576 A1 * | 10/2005 | Yagi | ........................ | G01J 1/429 250/372 |
| 2012/0303282 A1 * | 11/2012 | Jou | ....................... | G01J 3/0264 702/19 |
| 2012/0319593 A1 * | 12/2012 | Jou | ..................... | H05B 33/0869 315/152 |
| 2013/0040276 A1 * | 2/2013 | Takakura | ............. | A61N 5/0618 434/335 |
| 2013/0328501 A1 * | 12/2013 | Moriuchi | ........... | H05B 37/0272 315/294 |

(Continued)

OTHER PUBLICATIONS

Brainard et. al, "Action Spectrum for Melatonin Regulation in Humans: Evidence for a Novel Circadian Photoreceptor" Neuroscience , 21(16), pp. 6405-6412, 2001 (Year: 2001).*

(Continued)

*Primary Examiner* — Dominic J Bologna

(57) ABSTRACT

Disclosures of the present invention describe a device for measuring melatonin suppression induced by light source. The device consists of a light receiving unit, a pre-processor, a main processor, and a display unit. In the main processor, a first action spectrum generating unit is provided to convert a first light spectrum to first action spectrum, a second action spectrum generating unit is installed for converting a second light spectrum to second action spectrum, and a spectrum integrating unit is configured to produce a total action spectrum by integrating the first action spectrum with the second action spectrum. Therefore, the total action spectrum is evidenced can be used for describing the melatonin suppression power of both a short-wavelength light (<460 nm) and the long-wavelength light by high correctness.

14 Claims, 8 Drawing Sheets

(56) References Cited

U.S. PATENT DOCUMENTS

2016/0123802 A1* 5/2016 Likovich .............. G01J 1/0271
356/221
2019/0192878 A1* 6/2019 Lang .................... A61N 5/0618

OTHER PUBLICATIONS

Thapan et. al, "An action spectrum for melatonin suppression: evidence for a novel non-rod, non-cone photoreceptor system in humans" Journal of Physiology, 535, pp. 261-267, 2008 (Year: 2008).*

Hanifin et. al, "High-intensity red light suppresses melatonin" Chronobiology International, vol. 23, pp. 251-268, 2006 (Year: 2006).*

* cited by examiner

DEVICE FOR MEASURING MELATONIN SUPPRESSION INDUCED BY LIGHT SOURCE

BACKGROUND OF THE INVENTION

1. Field of the Invention

The present invention relates to the technology field of physical phenomenon quantizing devices, and more particularly to a device for measuring melatonin suppression induced by light source.

2. Description of the Prior Art

In human body, pineal gland or epiphysis synthesizes and secretes melatonin, a structurally simple hormone that communicates information about environmental lighting to various parts of the body. Melatonin is found to have important effects on physiological functions of human body. First of all, melatonin has a modulatory influence on sleep onset and maintenance. Secondly, clinic studies have reported that lack of melatonin for a long time may affect personal emotion, and lead to the occurrence of mood disorders more seriously. Thirdly, melatonin may affect hypothalamus on secreting gonadal releasing hormones, and also exhibit the effect of gonadal releasing hormones on pituitary gland. Last but not least, melatonin is also found to induce the synthesis of T lymphocytes and the release of interleukin-2 (IL-2) and interleukin-4 (IL-4), so as to increase the immunity of human body.

Literatures 1, 2 and 3 have reported that melatonin has a higher sensitivity as retina is exposed under a visible light with short wavelength. Moreover, the studies have also presented that broad spectrum, polychromatic fluorescent light enriched in the short-wavelength portion of the visible spectrum is more potent for pineal melatonin suppression in healthy men and women. Herein, literature 1 is written by Brainard et. al, and is entitled with "Action Spectrum for Melatonin Regulation in Humans: Evidence for a Novel Circadian Photoreceptor" and published on Neuroscience, 21(16), pp. 6405-6412, 2001. Moreover, literature 2 is written by Thapan et. al, and is entitled with "An action spectrum for melatonin suppression: evidence for a novel non-rod, non-cone photoreceptor system in humans" and published on Journal of Physiology, 535, pp. 261-267, 2008. On the other hand, literature 3 is written by Hanifin et. al, and is entitled with "High-intensity red light suppresses melatonin" and published on Chronobiology International, Vol. 23, pp. 251-268, 2006.

After reading the three literatures, it is understood that photons of short-wavelength light possess higher melatonin suppression power than that of long-wavelength light in a unit lumen. However, there is still unknown that how to quantize the melatonin suppression power of a visible light. Accordingly, U.S. Pat. No. 8,812,424 B2 discloses a melatonin suppression extent measuring device, which is able to receive and process a light to a spectral data, so as to further process the spectral data to a percent value of melatonin suppression based on parameters of reference wavelength parameter and a reference quanta.

The melatonin suppression extent measuring device can be used for quantize the melatonin suppression power of a long-wavelength light and even a short-wavelength light. During quantizing the melatonin suppression power of the short-wavelength light, a main processor of the melatonin suppression extent measuring device is configured to generate a specific action spectrum for describing the melatonin suppression power of the short-wavelength light (<460 nm). However, it is challenged that the generated specific action spectrum may not be completely correct.

From above descriptions, it is understood that the melatonin suppression extent measuring device still has room for improvement. In view of that, inventors of the present application have made great efforts to make inventive research thereon and eventually provided a device for measuring melatonin suppression induced by light source.

SUMMARY OF THE INVENTION

The primary objective of the present invention is to provide a device for measuring melatonin suppression induced by light source. The device consists of a light receiving unit, a pre-processor, a main processor, and a display unit. In the main processor, a first action spectrum generating unit is provided to convert a first light spectrum to first action spectrum, a second action spectrum generating unit is installed for converting a second light spectrum to second action spectrum, and a spectrum integrating unit is configured to produce a total action spectrum by integrating the first action spectrum with the second action spectrum. Therefore, the total action spectrum is evidenced can be used for describing the melatonin suppression power of both a short-wavelength light (<460 nm) and a long-wavelength light by high correctness.

In order to achieve the primary objective of the present invention, the inventor of the present invention provides one embodiment for the device for measuring melatonin suppression induced by light source, comprising:

a light receiving module, being used for receiving a visible light from a light source, and having a spectrum conversion unit for converting the received visible light to a spectrum data comprising a first light spectrum and a second light spectrum for respectively describing a long-wavelength part and a short-wavelength part of the visible light; and a controlling and processing module, being adopted for controlling the light receiving module to receive the visible light so as to get the spectrum data from the light receiving module, and comprising:

a first action spectrum generating unit for converting the first light spectrum to a first action spectrum;

a second action spectrum generating unit for converting the second light spectrum to a second action spectrum; and a spectrum integrating unit for producing a total action spectrum by integrating the first action spectrum with the second action spectrum.

Furthermore, in order to achieve the primary objective of the present invention, the inventor of the present invention further provides another one embodiment for the device for measuring melatonin suppression induced by light source, comprising:

a pre-processor, being electrically connected to the light receiving unit, and having a spectrum conversion unit for convert the received visible light to a spectrum data comprising a first light spectrum and a second light spectrum for respectively describing a long-wavelength part and a short-wavelength part of the visible light;

a main processor, being electrically connected to the pre-processor, and comprising:

a first action spectrum generating unit for converting the first light spectrum to a first action spectrum;

a second action spectrum generating unit for converting the second light spectrum to a second action spectrum; and a spectrum integrating unit for producing a total action spectrum by integrating the first action spectrum with the second action spectrum; and a display unit, being electrically connected to the main processor for showing the first action spectrum, the second action spectrum or the total action spectrum.

It is worth further explaining that, both the two embodiments of the melatonin suppression power measuring device described above are able to be integrated into a smart meter device or a controlling console of a smart lighting device.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein.

DETAILED DESCRIPTION OF THE PREFERRED EMBODIMENTS

To more clearly describe a device for measuring melatonin suppression induced by light source according to the present invention, embodiments of the present invention will be described in detail with reference to the attached drawings hereinafter.

First Embodiment

Figure 1:
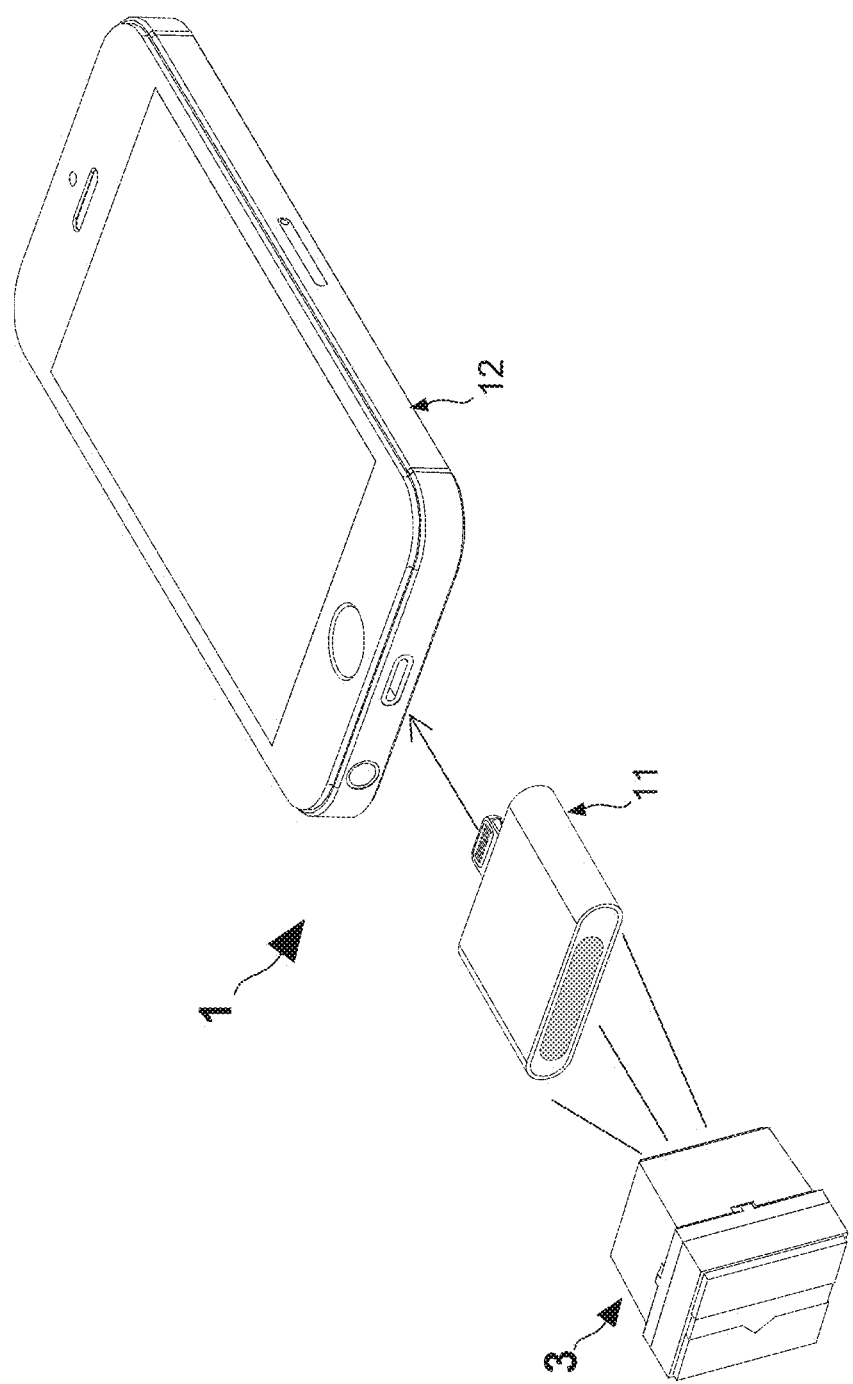
FIG. 1 shows a stereo diagram of a first embodiment of a device for measuring melatonin suppression induced by light source according to the present invention.
Figure 2:
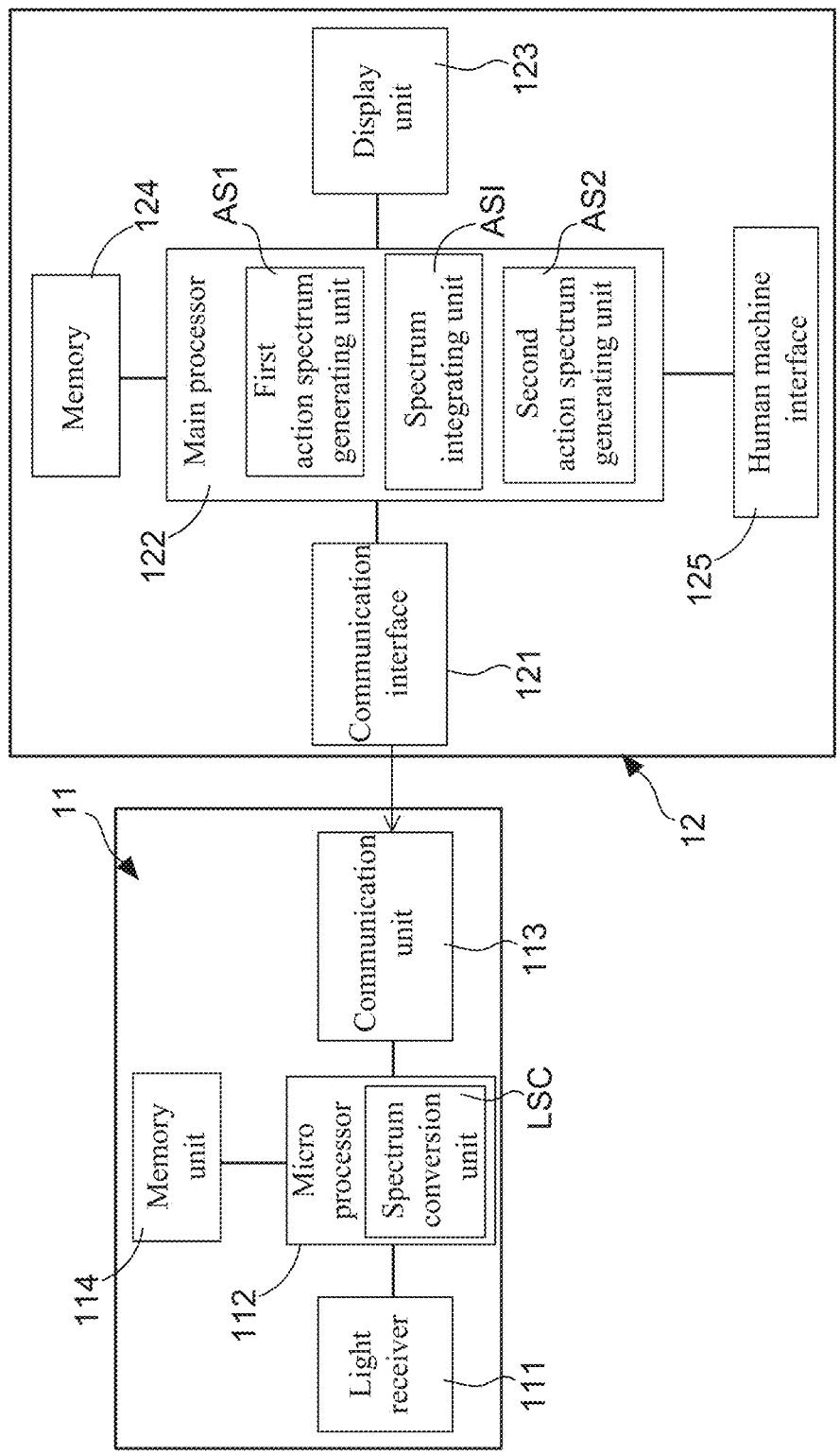
FIG. 2 shows a circuit block diagram of the first embodiment of the device for measuring melatonin suppression induced by light source.

With reference to FIG. 1, there is provided a stereo diagram of a first embodiment of a device for measuring melatonin suppression induced by light source according to the present invention. Moreover, FIG. 2 shows a circuit block diagram of the first embodiment of the device for measuring melatonin suppression induced by light source. The present invention particularly provides a melatonin suppression power measuring device 1, which mainly comprises: a light receiving module 11 and a controlling and processing module 12. From the first embodiment shown in FIG. 1 and FIG. 2, it is clear that the controlling and processing module 12 is but not limited to be a smart phone. The controlling and processing module 12 can also be an electronic device having microprocessor or main processor, such as desk PC, laptop PC, tablet PC, or smart watch. In the present invention, the light receiving module 11 comprises: a light receiver 111, a microprocessor 112 electrically connected to the light receiver 111, a communication unit 113 electrically connected to the microprocessor 112, and a memory unit 114 electrically connected to the microprocessor 112. By the controlling of the controlling and processing module 12, the light receiving module 11 is able to receive a visible light from a light source 3. Particularly, a spectrum conversion unit LSC is provided in the microprocessor 112 of the light receiving module 11, and is configured for converting the received visible light to a spectrum data comprising a first light spectrum and a second light spectrum for respectively describing a long-wavelength part and a short-wavelength part of the visible light.

On the other hand, the controlling and processing module 12 comprises: a communication interface 121 for communicating with the communication unit 113, a main processor 122 electrically connected to the communication interface 121, a display unit 123 electrically connected to the main processor 122, a memory 124 electrically connected to the main processor 122, and a human machine interface (HMI) 125 electrically connected to the main processor 122. It is easy to know that the communication interface 121 makes the main processor 122 be able to receive the spectrum data from the light receiving module 11. Particularly, in the present invention, the main processor 122 is provided with a first action spectrum generating unit AS1, a second action spectrum generating unit AS2 and a spectrum integrating unit ASI therein. The first action spectrum generating unit AS1 is configured for converting the first light spectrum to a first action spectrum, and the second action spectrum generating unit AS2 is used for converting the second light spectrum to a second action spectrum. Moreover, the spectrum integrating unit ASI is adopted for producing a total action spectrum by integrating the first action spectrum with the second action spectrum.

Herein, it needs to further explain that, the first action spectrum generating unit AS1 converts the first light spectrum to the first action spectrum by the use of conversion functions (1), (2) and (3), and the second action spectrum generating unit AS2 converts the second light spectrum to the second action spectrum by the use of conversion functions (1'), (2) and (3). The above-mentioned conversion functions are listed as follows.

$$S_{PQ}(\lambda) = 10^{(\lambda - \lambda r)/Fl} \tag{1}$$

$$S_{PQ}(\lambda) = 0.15975 + 0.84832 \times e^{\left(-0.5 \times \left(\frac{\lambda - \lambda r}{29}\right)^2\right)} \tag{1'}$$

$$S_{PQC}(\lambda) = \left[\int S_{PQ}(\lambda) S_I(\lambda) d\lambda\right] / \left[\int \lambda S_I(\lambda) d\lambda\right] \tag{2}$$

$$S_{PLC}(\lambda) = \left[\int S_{PQ}(\lambda) S_I(\lambda) d\lambda\right] / \left[\int S_I(\lambda) d\lambda\right] \tag{3}$$

Moreover, function notations and variable notations used in above-presented conversion functions are summarized in following Table (1).

TABLE 1

| Notations | Description |
|---|---|
| $S_{PQ}(\lambda)$ | A function of melatonin suppression power per quanta for a given monochromatic light |
| $S_{PQC}(\lambda)$ | A function of correlated melatonin suppression power per quanta for a given polychromatic light |
| $S_{PLC}(\lambda)$ | A function of melatonin suppression power per lumen for a polychromatic light, |
| $S_f(\lambda)$ | Spectrum data |
| $\lambda$ | Measured wavelength |
| $\lambda r$ | Reference optical wavelength (480 nm) |
| FI | A fitting index in a range from 70 to 100 (such as 75) |

Referring to FIG. 1 and FIG. 2 again, in which memory 124 is used for storing the first action spectrum, the second action spectrum or the total action spectrum. Moreover, the display unit 123 is controlled by the main processor 122 or a graphics processing unit (GPU) to show the first action spectrum, the second action spectrum or the total action spectrum. Of course, a user is able to operate or control the controlling and processing module 12 through the HMI 125, so as to make the melatonin suppression power measuring device 1 complete a quantization of a melatonin suppression power of a specific visible light radiated from a specific light source 3. In addition, it is noted that the human machine interface (HMI) 125 and the display unit 123 can be integrated to form a touch display device.

Experimental Data

Figure 3:
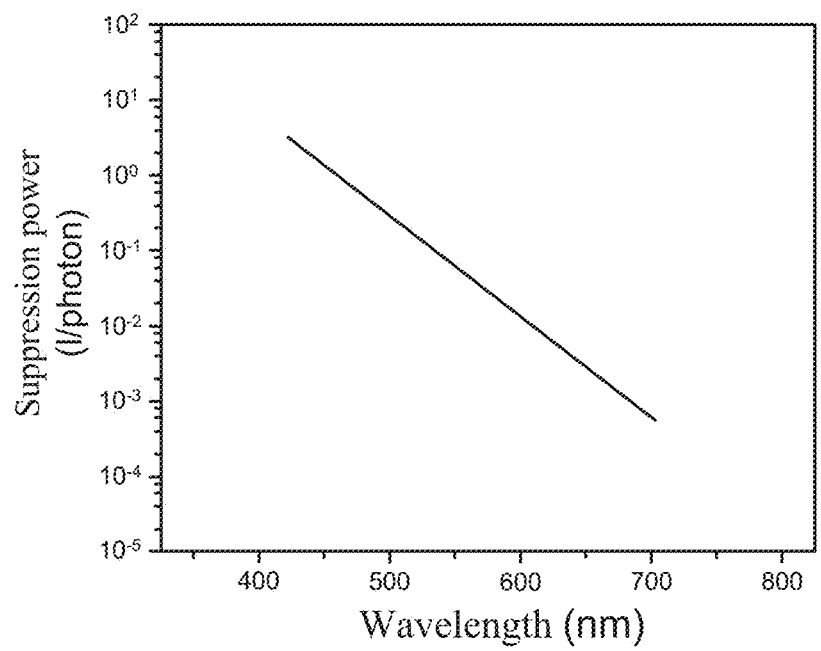
FIG. 3 shows a curve graph of wavelength versus a function of melatonin suppression power per quanta.
Figure 4:
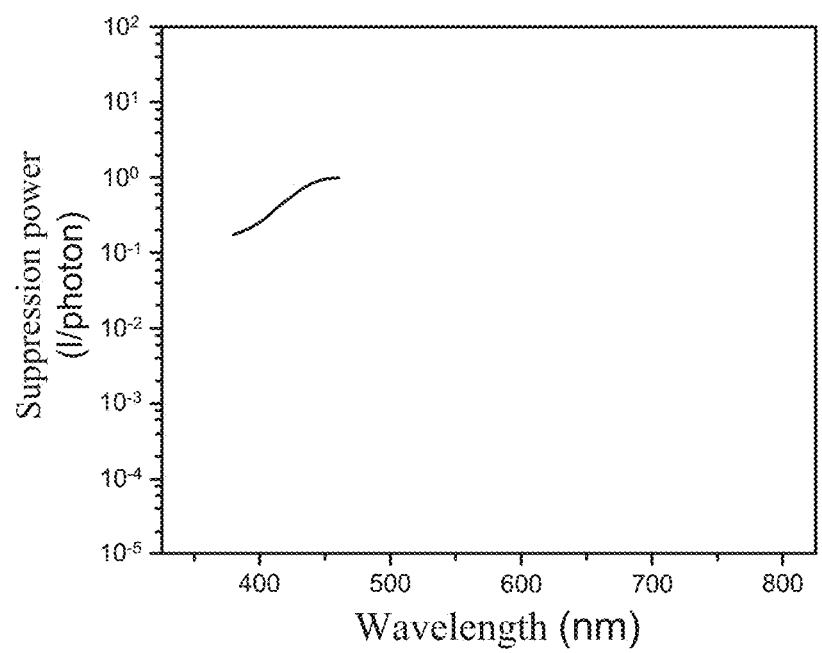
FIG. 4 shows a curve graph of wavelength versus a function of melatonin suppression power per quanta.
Figure 5:
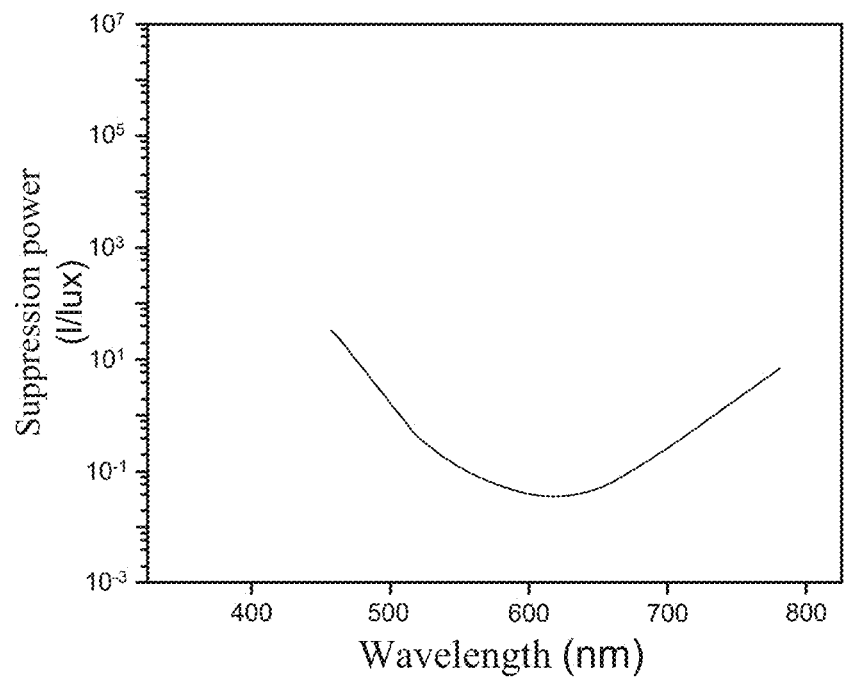
FIG. 5 shows a curve graph of wavelength versus a function of melatonin suppression power per lumen.
Figure 6:
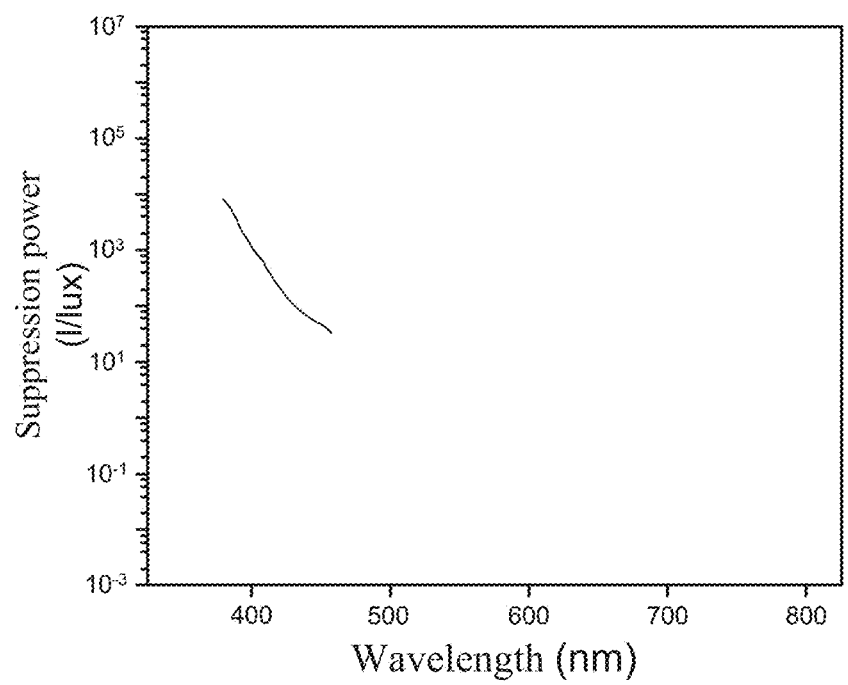
FIG. 6 shows a curve graph of wavelength versus a function of melatonin suppression power per lumen.
Figure 7:
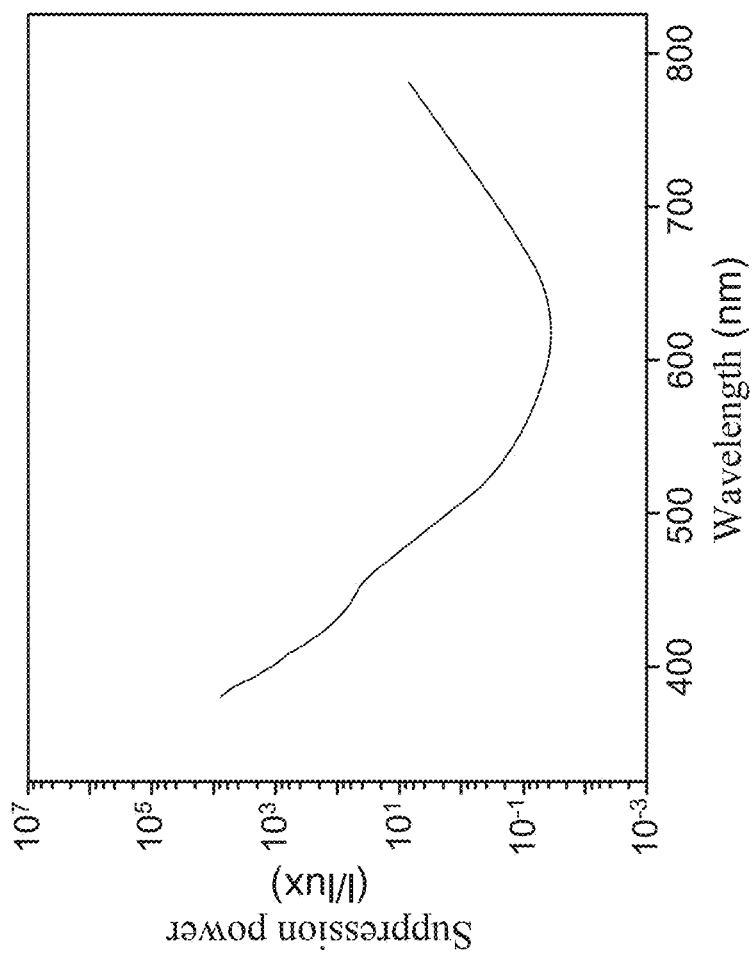
FIG. 7 shows a curve graph of wavelength versus a function of melatonin suppression power per lumen.

FIG. 3 and FIG. 4 show two curve graphs of wavelength versus a function of melatonin suppression power per quanta. On the other hand, FIG. 5, FIG. 6 and FIG. 7 show three curve graphs of wavelength versus a function of melatonin suppression power per lumen. During the conversion of the first action spectrum, the first action spectrum generating unit AS1 firstly loads the spectrum data received from the light receiving module 11 into the conversion function (1), and then loads the spectrum data into the conversion function (3). As a result, two curve graphs are obtained and shown as FIG. 3 and FIG. 5, respectively. Moreover, during the conversion of the second action spectrum, the second action spectrum generating unit AS2 firstly loads the spectrum data received from the light receiving module 11 into the conversion function (1'), and then loads the spectrum data into the conversion function (3). Consequently, two curve graphs are obtained and shown as FIG. 4 and FIG. 6, respectively. Therefore, a total action spectrum is eventually produced by the spectrum integrating unit ASI through the way of integrating the first action spectrum of FIG. 5 with the second action spectrum of FIG. 6.

Following Table (2) records measurement data of melatonin suppression extent of various light sources. From the measurement data of Table (2), it is found that, each of the extent values of melatonin suppression measured by this melatonin suppression power measuring device 1 shows almost no discrepancies after being compared to that of the device disclosed by U.S. Pat. No. 8,812,242 B2. Therefore, the experimental data have proved that, the melatonin suppression power measuring device 1 of the present invention can be used to produce a total action spectrum for describing the melatonin suppression power of both a short-wavelength light (<460 nm) and a long-wavelength light by high correctness.

TABLE 2

| | Melatonin suppression extent Measurement is carried out by using: | |
|---|---|---|
| Light source | (1) device disclosed by U.S. Pat. No. 8,812,242 B2 | (2) device of the present invention |
| LED (6,067K) | 6% | 4% |
| CFL (5,871K) | 6.9% | 3.6% |
| OLED (4,033K) | 3% | 2.4% |
| OLED (3,034K) | 1.6% | 1.6% |
| LED (2,770K) | 1.8% | 1.6% |
| CFL (2,588K) | 3.1% | 1.1% |
| OLED (2,120K) | 0.8% | 0.8% |
| LED (2,020K) | 0.9% | 0.9% |

Second Embodiment

Figure 8:
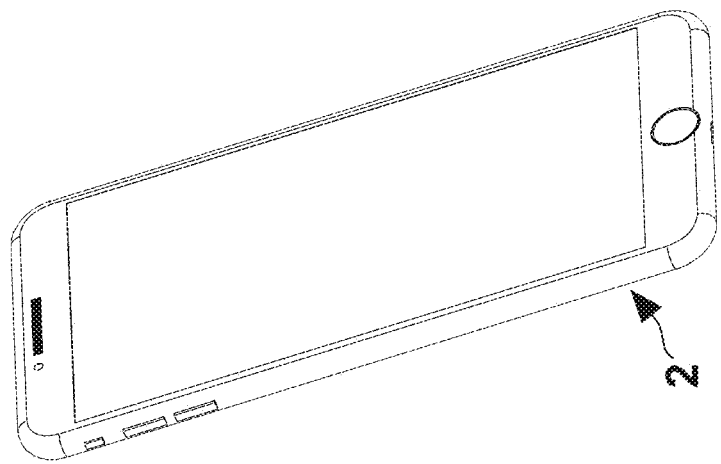
FIG. 8 shows a stereo diagram of a second embodiment of the device for measuring melatonin suppression induced by light source according to the present invention.
Figure 8:
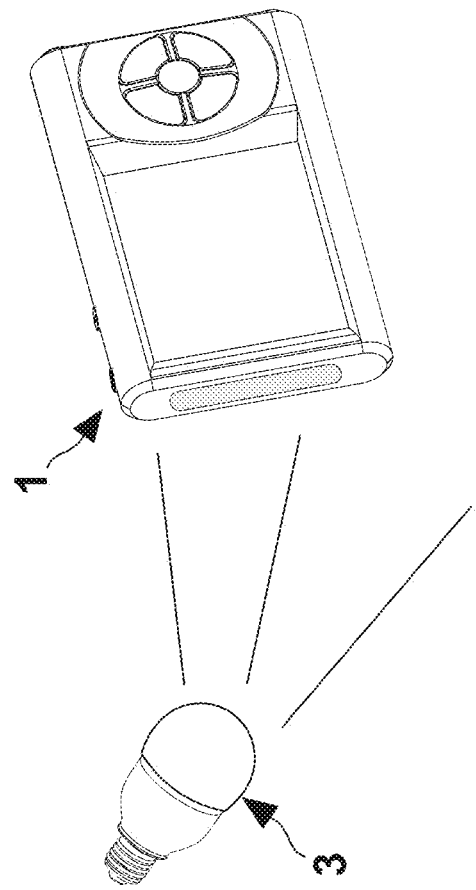
Figure 9:
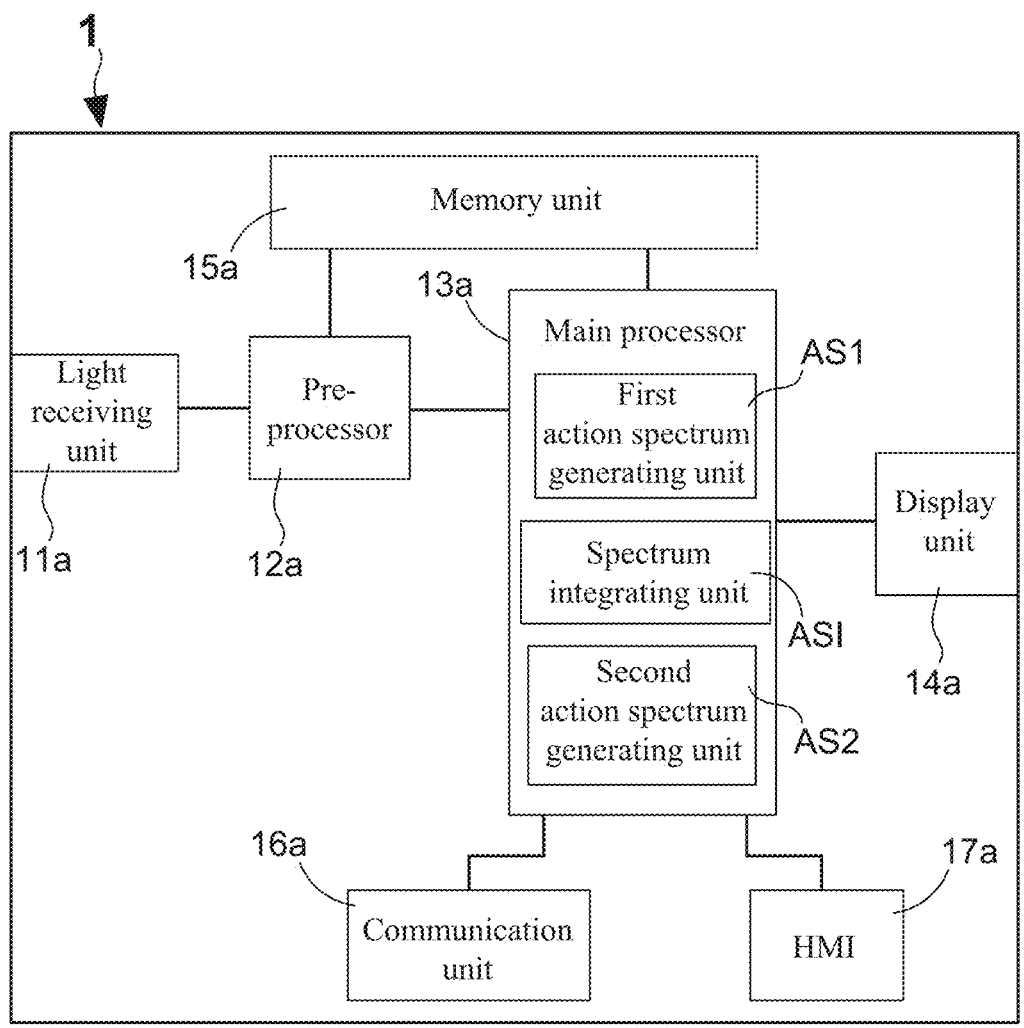
FIG. 9 shows a circuit block diagram of the second embodiment of the device for measuring melatonin suppression induced by light source.

With reference to FIG. 8, there is provided a stereo diagram of a second embodiment of the device for measuring melatonin suppression induced by light source according to the present invention. Moreover, FIG. 9 shows a circuit block diagram of the second embodiment of the device for measuring melatonin suppression induced by light source. The present invention particularly also provides a second embodiment of the melatonin suppression power measuring device 1, which mainly comprises: a light receiving unit 11a, a pre-processor 12a electrically connected to the light receiving unit 11a, a main processor 13a electrically connected to the pre-processor 12a, a memory unit 15a electrically connected to the pre-processor 12a and the main processor 13a, a display unit 14a electrically connected to the main processor 13a, a communication unit 16a electrically connected to the main processor 13a, and a human machine interface (HMI) 17a electrically connected to the main processor 13a.

By the controlling of the pre-processor 12a, the light receiving unit 11a is able to receive a visible light from a light source 3. Particularly, a spectrum conversion unit is provided in the pre-processor for converting the received visible light to a spectrum data comprising a first light spectrum and a second light spectrum for respectively describing a long-wavelength part and a short-wavelength part of the visible light. Moreover, the main processor 13a is provided with a first action spectrum generating unit AS1, a second action spectrum generating unit AS2 and a spectrum integrating unit ASI therein. The first action spectrum generating unit AS1 is configured for converting the first light spectrum to a first action spectrum, and the second action spectrum generating unit AS2 is used for converting the second light spectrum to a second action spectrum. Moreover, the spectrum integrating unit ASI is adopted for producing a total action spectrum by integrating the first action spectrum with the second action spectrum.

It is easy to know that the memory unit 15a is used for storing the spectrum data, the first action spectrum, the second action spectrum, and the total action spectrum. On the other hand, the display unit 14a is controlled by the main processor 13a or a graphics processing unit (GPU) to show the first action spectrum, the second action spectrum or the total action spectrum. Of course, a user is able to operate or control the melatonin suppression power measuring device 1 through the HMI 17a, so as to make the melatonin suppression power measuring device 1 complete a quantization of a melatonin suppression power of a specific visible light radiated from a specific light source 3. In addition, FIG. 8 also depicts that the communication unit 16a makes the main processor 123a be able to communicate with an electronic device 2 like smart phone. The electronic device 2 can also be a desk PC, a laptop PC, a tablet PC, or a smart watch.

Third Embodiment

Figure 10:
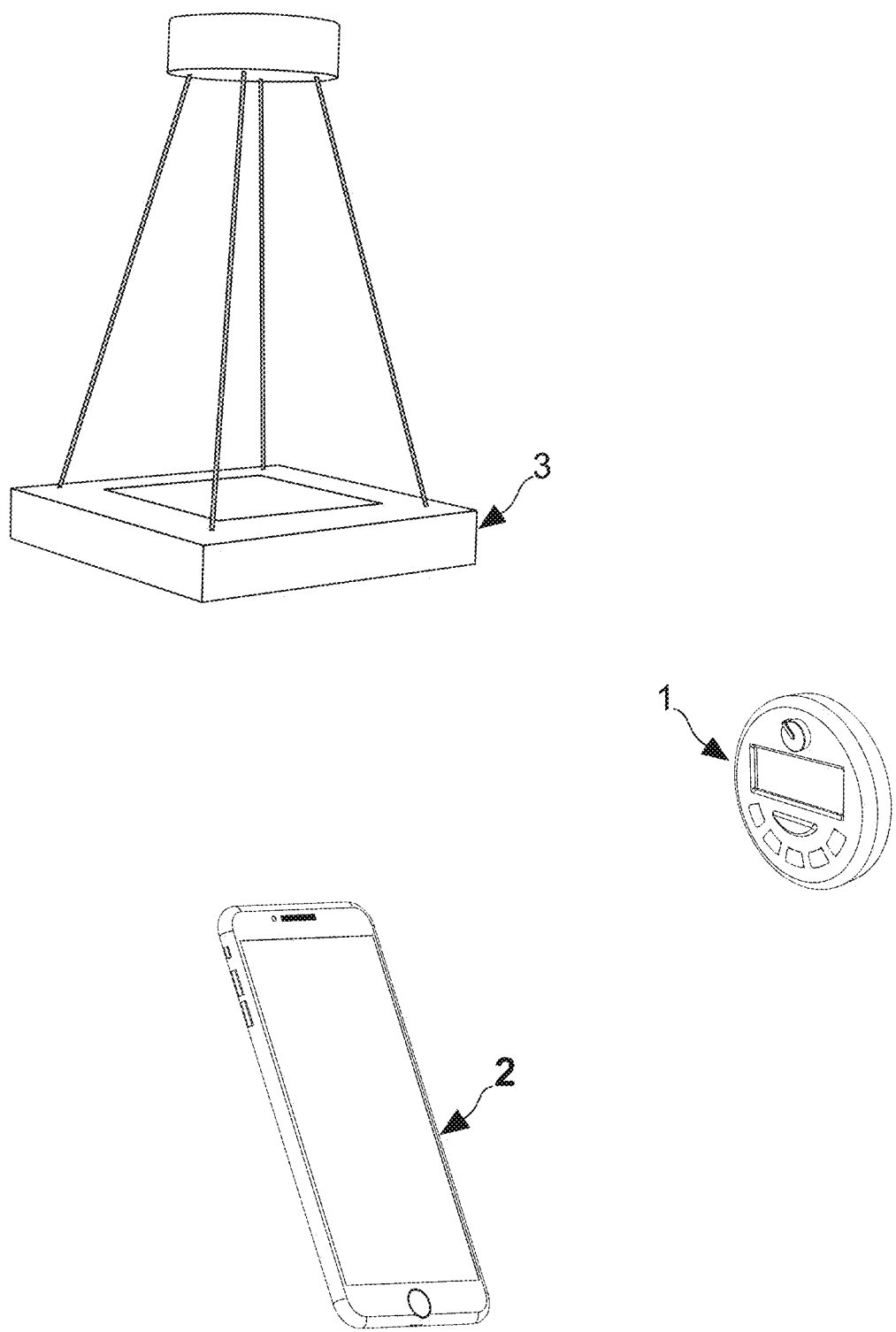
FIG. 10 shows a stereo diagram of a third embodiment of the device for measuring melatonin suppression induced by light source according to the present invention.

FIG. 10 shows a stereo diagram of a third embodiment of the device for measuring melatonin suppression induced by light source according to the present invention. The present invention particularly further provides a second embodiment of the melatonin suppression power measuring device 1, which is able to be integrated into a smart meter device or a controlling console of a smart lighting device.

Therefore, through above descriptions, the device for measuring melatonin suppression induced by light source provided by the present invention has been introduced completely and clearly; in summary, the present invention includes the advantages of:

(1) The present invention particularly provides a device for measuring melatonin suppression induced by light source. The device mainly comprises: of a light receiving unit 11a, a pre-processor 12a, a main processor 13a, and a display unit 14a. In the main processor 13a, a first action spectrum generating unit AS1 is provided to convert a first light spectrum to first action spectrum, a second action spectrum generating unit AS2 is installed for converting a second light spectrum to second action spectrum, and a spectrum integrating unit ASI is configured to produce a total action spectrum by integrating the first action spectrum with the second action spectrum.

(2) In addition, experimental data have proved that, the melatonin suppression power measuring device 1 of the present invention can be used to produce a total action spectrum for describing the melatonin suppression power of both a short-wavelength light (<460 nm) and a long-wavelength light by high correctness.

The above description is made on embodiments of the present invention. However, the embodiments are not intended to limit scope of the present invention, and all equivalent implementations or alterations within the spirit of the present invention still fall within the scope of the present invention.

What is claimed is:

1. A melatonin suppression power measuring device, comprising:
    a light receiving module, being configured for receiving a visible light from a light source, and having a spectrum conversion unit for converting the received visible light to a spectrum data comprising a first light spectrum and a second light spectrum for respectively describing a long-wavelength part and a short-wavelength part of the visible light; and
    a controlling and processing module, being adapted to control the light receiving module to receive the visible light so as to get the spectrum data from the light receiving module, and comprising:
        a first action spectrum generating unit for converting the first light spectrum to a first action spectrum;
        a second action spectrum generating unit for converting the second light spectrum to a second action spectrum; and
        a spectrum integrating unit for producing a total action spectrum by integrating the first action spectrum with the second action spectrum.

2. The melatonin suppression power measuring device of claim 1, wherein the light receiving module comprises:
    a light receiver;
    a microprocessor, being electrically connected to the light receiver and having the spectrum conversion unit;
    a communication unit, being electrically connected to the microprocessor, and being adapted to make the light receiving module be able to communicate with the controlling and processing module; and
    a memory unit, being electrically connected to the microprocessor for storing the spectrum data.

3. The melatonin suppression power measuring device of claim 2, wherein the controlling and processing module comprises:
    a communication interface for communicating with the communication unit;
    a main processor, being electrically connected to the communication interface and having the first action spectrum generating unit, the second action spectrum generating unit and the spectrum integrating unit;
    a display unit, being electrically connected to the main processor for showing the first action spectrum, the second action spectrum or the total action spectrum; and
    a memory, being electrically connected to the main processor for storing the first action spectrum, the second action spectrum or the total action spectrum.

4. The melatonin suppression power measuring device of claim 3, wherein the controlling and processing module further comprises a human machine interface (HMI) electrically connected to the main processor.

5. The melatonin suppression power measuring device of claim 4, wherein the human machine interface (HMI) and the display unit are integrated to form a touch display device.

6. The melatonin suppression power measuring device of claim 1, wherein the first action spectrum generating unit converts the first light spectrum to the first action spectrum by the use of following three conversion functions:
    (1) $S_{PQ}(\lambda)$, being defined as a function of melatonin suppression power per quanta for a given monochromatic light, and being equal to $10(\lambda-\lambda r)/FI$; wherein $\lambda$, $\lambda r$ and $FI$ are a wavelength of the visible light, a reference optical wavelength and a fitting index, respectively;
    (2) $S_{PQC}(\lambda)$, being defined as a function of correlated melatonin suppression power per quanta for a given polychromatic light, and being equal to $[\int S_{PQ}(\lambda)S_f(\lambda)d\lambda]/[\int \lambda S_f(\lambda)d\lambda]$; wherein $S_f(\lambda)$ is defined as a function of experimentally measured spectral intensity; and
    (3) $S_{PLC}(\lambda)$, defined as a function of melatonin suppression power per lumen for a polychromatic light, and being equal to $[\int S_{PQ}(\lambda)S_f(\lambda)d\lambda]/[\int S_f(\lambda)d\lambda]$.

7. The melatonin suppression power measuring device of claim 1, wherein the second action spectrum generating unit converts the second light spectrum to the second action spectrum by the use of following three conversion functions:
    (1) $S_{PQ}(\lambda)$, being defined as a function of melatonin suppression power per quanta for a given monochromatic light, and being equal to $$0.15975 + 0.84832\left(e^{-0.5\left(\frac{\lambda-\lambda r}{29}\right)^2}\right);$$

wherein λ and λr are a wavelength of the visible light and a reference optical wavelength, respectively;

(2) $S_{PQC}(\lambda)$, being defined as a function of correlated melatonin suppression power per quanta for a given polychromatic light, and being equal to $[\int S_{PQ}(\lambda)S_f(\lambda)d\lambda]/[\int \lambda S_f(\lambda)d\lambda]$; wherein $S_f(\lambda)$ is defined as a function of experimentally measured spectral intensity; and (3) $S_{PLC}(\lambda)$, defined as a function of melatonin suppression power per lumen for a polychromatic light, and being equal to $[\int S_{PQ}(\lambda)S_f(\lambda)d\lambda]/[\int S_f(\lambda)d\lambda]$.

8. The 1 melatonin suppression power measuring device of claim 1, wherein the controlling and processing module is selected from the group consisting of desk PC, laptop PC, tablet PC, smart phone, and smart watch.

9. A melatonin suppression power measuring device, comprising:
- a light receiving unit for receiving a visible light from a light source;
- a pre-processor, being electrically connected to the light receiving unit, and having a spectrum conversion unit for converting the received visible light to a spectrum data comprising a first light spectrum and a second light spectrum for respectively describing a long-wavelength part and a short-wavelength part of the visible light;
- a main processor, being electrically connected to the pre-processor, and comprising:
  - a first action spectrum generating unit for converting the first light spectrum to a first action spectrum;
  - a second action spectrum generating unit for converting the second light spectrum to a second action spectrum; and
  - a spectrum integrating unit for producing a total action spectrum by integrating the first action spectrum with the second action spectrum; and
- a display unit, being electrically connected to the main processor for showing the first action spectrum, the second action spectrum or the total action spectrum.

10. The melatonin suppression power measuring device of claim 9, further comprising:
- a memory unit, being electrically connected to the pre-processor and the main processor for storing the spectrum data, the first action spectrum, the second action spectrum, and the total action spectrum;
- a communication unit, being electrically connected to the main processor, and being adapted to make the main processor be able to communicate with an electronic device; and
- a human machine interface (HMI), being electrically connected to the main processor.

11. The melatonin suppression power measuring device of claim 10, wherein the human machine interface (HMI) and the display unit are integrated to form a touch display device.

12. The melatonin suppression power measuring device of claim 10, wherein the electronic device is selected from the group consisting of desk PC, laptop PC, tablet PC, smart phone, and smart watch.

13. The melatonin suppression power measuring device of claim 9, wherein the first action spectrum generating unit converts the first light spectrum to the first action spectrum by the use of following three conversion functions:

(1) $S_{PQ}(\lambda)$, being defined as a function of melatonin suppression power per quanta for a given monochromatic light, and being equal to $10(\lambda-\lambda r)/FI$; wherein λ, λr and FI are a wavelength of the visible light, a reference optical wavelength and a fitting index, respectively;

(2) $S_{PQC}(\lambda)$, being defined as a function of correlated melatonin suppression power per quanta for a given polychromatic light, and being equal to $[\int S_{PQ}(\lambda)S_f(\lambda)d\lambda]/[\int \lambda S_f(\lambda)d\lambda]$; wherein $S_f(\lambda)$ is defined as a function of experimentally measured spectral intensity; and (3) $S_{PLC}(\lambda)$, defined as a function of melatonin suppression power per lumen for a polychromatic light, and being equal to $[\int S_{PQ}(\lambda)S_f(\lambda)d\lambda]/[\int S_f(\lambda)d\lambda]$.

14. The melatonin suppression power measuring device of claim 9, wherein the second action spectrum generating unit converts the second light spectrum to the second action spectrum by the use of following three conversion functions:

(1) $S_{PQ}(\lambda)$, being defined as a function of melatonin suppression power per quanta for a given monochromatic light, and being equal to $$0.15975 + 0.84832\left(e^{-0.5\left(\frac{\lambda-\lambda r}{29}\right)^2}\right);$$

wherein λ and λr are a wavelength of the visible light and a reference optical wavelength, respectively;

(2) $S_{PQC}(\lambda)$, being defined as a function of correlated melatonin suppression power per quanta for a given polychromatic light, and being equal to $[\int S_{PQ}(\lambda)S_f(\lambda)d\lambda]/[\int \lambda S_f(\lambda)d\lambda]$; wherein $S_f(\lambda)$ is defined as a function of experimentally measured spectral intensity; and (3) $S_{PLC}(\lambda)$, defined as a function of melatonin suppression power per lumen for a polychromatic light, and being equal to $[\int S_{PQ}(\lambda)S_f(\lambda)d\lambda]/[\int S_f(\lambda)d\lambda]$.

* * * * *